United States Patent
Borodic

(10) Patent No.: US 7,270,826 B2
(45) Date of Patent: Sep. 18, 2007

(54) **METHODS OF USING *BOTULINUM* TOXIN FOR THE TREATMENT OF HYPERVOLEMIC LIP DEFORMITY (LIP ECTROPION)**

(76) Inventor: Gary E. Borodic, 90 Kensington Dr., Canton, MA (US) 02021

( * ) Notice: Subject to any disclaimer, the term of this patent is extended or adjusted under 35 U.S.C. 154(b) by 0 days.

(21) Appl. No.: 11/028,600

(22) Filed: Jan. 5, 2005

(65) Prior Publication Data

US 2005/0208075 A1    Sep. 22, 2005

Related U.S. Application Data

(60) Provisional application No. 60/534,330, filed on Jan. 5, 2004.

(51) Int. Cl.
*A61K 39/08* (2006.01)
*A61K 38/00* (2006.01)
*C07K 14/00* (2006.01)

(52) U.S. Cl. .............. 424/239.1; 424/236.1; 424/9.1; 514/2; 514/12; 530/350; 435/252.7

(58) Field of Classification Search ............. 424/239.1, 424/236.1, 9.1; 514/2, 12; 530/350; 435/252.7
See application file for complete search history.

(56) References Cited

FOREIGN PATENT DOCUMENTS

| CA | 2280565 | 2/2001 |
|---|---|---|
| WO | WO 2004/060384 A2 | 7/2004 |

OTHER PUBLICATIONS

Fagien, S., Botox for the Treatment of Dynamic and Hyperkinetic Facial Lines and Furrows: Ajunctive use in facial Aesthetic Surgery. Plastic and Reconstructive Surgery 103 (2), 701-713 (Feb. 1999).*
Rapaport et al. , Movement Disorders 15, 352-355 (2000).*
Moller et al. , Oral Surgery, oral medicine, oral pathology, oral radiology and endodontices 96, 544-549 (Nov. 2003).*
Fagien, Steven, "Botulinum Toxin Type A for Facial Asthetic Enhancement: Role in Facial Shaping", Plastic and Reconstructive Surgery, Oct. Supplement 2003, XP008046806, vol. 112 (5) pp. 65-205.
Kane, Michael A.C., "The Effect of Botulinum Toxin Injections on the Nasolabial Fold", Plastic and Reconstructive Surgery, Oct. Supplement 2003, XP008046803, vol. 112 (5) Sup pp. 665-725.
Mataraso, Seth L. et al., "Treatment Guidelines for Botulinum Toxin Type A for the Periocular Region and a Report on Partial Upper Lip Ptosis Following Injections to the Lateral Canthal Rhytids", Plastic and Recostructive Surgery, Jul. 2001, XP008046805, vol. 108 (1), 208-217.
Sposito, M. Matilde, "New Indications for Botulinum Toxin Type A in Cosmetics: Mouth and Neck", Plastic and Reconstructive Surgery, Aug. 2002, XP008046793, vol. 110 (2), 601-613.
International Search Report for PCT/US2005/000117.

* cited by examiner

*Primary Examiner*—Chih-Min Kam
(74) *Attorney, Agent, or Firm*—Milbank, Tweed, Hadley & McCloy LLP

(57) ABSTRACT

The present invention uses pharmaceutical preparations of *Botulinum* toxin to induce neurogenic atrophy to alter muscle volume and subsequently, facial contour. Reduction in lip volume is accomplished using the disclosed methods thereby producing a favorable effect on a hypervolemic lip deformity. In other embodiments of the invention, the methods disclosed herein may be used to shrink muscle bulk and contour, especially in the face. In one embodiment, treating excessive muscle bulk below the eyelids can cause a smoothing of the lower lid and cheek contour producing a favorable improvement in appearance. Such an application is in distinct contrast to rhytide (wrinkle reduction) as the injected region does not contain wrinkles or any other form of dynamic line, merely excessive tissue bulk.

8 Claims, No Drawings

METHODS OF USING *BOTULINUM* TOXIN FOR THE TREATMENT OF HYPERVOLEMIC LIP DEFORMITY (LIP ECTROPION)

This application claims priority under 35 U.S.C. 119(e) to U.S. Provisional Application Ser. No. 60/534,330 filed Jan. 5, 2004. All references, patents and printed publications cited herein are hereby incorporated by reference in their entirety.

FIELD OF THE INVENTION

The invention is directed to methods of using *Botulinum* toxin to reduce the size and volume of hypervolemic lips. The invention is also directed to methods of using *Botulinum* toxin to reduce facial volume and alter facial contour, such as, for example, reducing excessive muscle bulk above or below the eyelid. The methods of the present invention may also be used to smooth the appearance of the eyelids, cheeks and/or jowels to produce a favorable improvement in appearance.

BACKGROUND

The *Botulinum* toxins comprise a group of zinc-dependent endopeptidases. Seven immunotypes of *Botulinum* neurotoxins have been characterized, these are referred to, respectively, as immunotypes A, B, C, D, E, F and G. The *Botulinum* toxins are capable of binding at the presynaptic membrane of the motor nerve axon terminal via its heavy chain, followed by internalization of the light chain. The light chain reacts with cellular substrates consisting of SNAP-25 (immunotype A), synaptobrevin (immunotype B) and syntaxin (immunotype C). The cytoplasmic cellular substrates of the *Botulinum* toxins are integral in exocytosis of neurotransmitters which are coupled to motor nerve conduction. By virtue of the long duration of neuromuscular blockade which is induced upon administration of *Botulinum* toxin to a subject, catabolism occurs within the innervated striated muscle.

The lips of the mouth, via attendant muscular groups, are an important component of the muscles used in facial expression. The muscles of facial expression are also important in non-verbal communication. Lip position may indicate anger, frustration, threat, fear, determination while pondering, thinking or feeling uncertain. The face may show obvious muscular tension (i.e., with the lips held tightly together) or less noticeable tension (i.e., with the lips parted and slightly tightened). Hence, lip position and related deformities play an important role in communication, as well as external and self perception of appearance. Furthermore, deformity of the lip is instantly noticeable to patients and all who interact with those who may be afflicted with a lip deformity.

The anatomy of the lip is very complex. The inner surface of each lip is connected in the middle line to the corresponding gum by a fold of mucous membrane, the frenulum, the upper being the larger. The Orbicularis oris muscle is not a simple sphincter muscle like the Orbicularis oculi; it consists of numerous strata of muscular fibers surrounding the orifice of the mouth, but having different direction. The Orbicularis oris muscle consists partly of fibers derived from the other facial muscles which are inserted into the lips, and partly of fibers proper to the lips. Of the former, a considerable number are derived from the Buccinator and form the deeper stratum of the Orbicularis. Some of the Buccinator fibers, namely, those near the middle of the muscle, decussate at the angle of the mouth, those arising from the maxilla passing to the lower lip, and those from the mandible to the upper lip. The uppermost and lowermost fibers of the Buccinator pass across the lips from side to side without decussation. Superficial to this stratum is a second, formed on either side by the Caninus and Triangularis, which cross each other at the angle of the mouth; those from the Caninus passing to the lower lip, and those from the Triangularis to the upper lip, along which they run, to be inserted into the skin near the median line. In addition to these, there are fibers from the Quadratus labii superioris, the Zygomaticus, and the Quadratus labii inferioris; these intermingle with the transverse fibers above described, and have principally an oblique direction.

The proper fibers of the lips are oblique, and pass from the under surface of the skin to the mucous membrane, through the thickness of the lip. Finally, there are fibers by which the muscle is connected with the maxillae and the septum of the nose above and with the mandible below. In the upper lip these consist of two bands, lateral and medial, on either side of the middle line; the lateral band (m. incisivus labii superioris) arises from the alveolar border of the maxilla, opposite the lateral incisor tooth, and arching laterally and is continuous with the other muscles at the angle of the mouth; the medial band (m. nasolabialis) connects the upper lip to the back of the septum of the nose. The interval between the two medial bands corresponds with the depression, called the philtrum, seen on the lip beneath the septum of the nose. The additional fibers for the lower lip constitute a slip (m. incisivus labii inferioris) on either side of the middle line; this arises from the mandible, lateral to the Mentalis, and intermingles with the other muscles at the angle of the mouth.

The Risorius arises in the fascia over the Masseter and, passing horizontally forward, superficial to the Platysma, is inserted into the skin at the angle of the mouth. It is a narrow bundle of fibers, broadest at its origin, but varies much in its size and form. Variations of the zygomatic head of the Quadratus labii superioris and Risorius are frequently absent and more rarely the Zygomaticus. The Zygomaticus and Risorius may be doubled or the latter greatly enlarged or blended with the Platysma. The muscles in this group are all supplied by the facial nerve.

The Orbicularis oris muscle, in its ordinary action, effects the direct closure of the lips. By its deep fibers, assisted by the oblique ones, it closely applies the lips to the alveolar arch. The superficial part, consisting principally of the decussating fibers, brings the lips together and also protrudes them forward. The Buccinators compress the cheeks, so that, during the process of mastication, the food is kept under the immediate pressure of the teeth. When the cheeks have been previously distended with air, the Buccinator muscles expel it from between the lips, as in blowing a trumpet; hence the name (buccina, a trumpet). The Risorius retracts the angle of the mouth, and produces an unpleasant grinning expression.

Hypervolemic lips, commonly known as "fat lips" are considered disfiguring by some people. Often, when the deformity is present, hypervolemic lips are considered out of proportion with other facial structures. Excessive exposure of the mucous membrane (the red portion of the lip) is characteristic of the deformity. Some populations of individuals, such as African-Americans, may exhibit a higher prevalence of high lip volume. The deformity may also be individual and sometimes associated with upper jaw or maxillary protrusion, or "buck tooth" deformity. For aesthetic reasons, some wish reduction of lip prominence and seek facial, oral or plastic surgeons to achieve changes in lip dimension.

Hypervolemic lips are anatomically caused by one or more of the following structural deviations: 1) Excessive tone of lip retractor function of certain facial muscles such as levator labii superioris, zygomaticus major and minor, levator labii inferioris, platysma, and depressor labii inferioris; 2) Excessive prominence and development of orbicularis oris muscle; 3) Excessive non-muscular soft tissue volume within the lip itself.

The retractors of the lip can, in part, cause rotation of the mucous membrane with excessive resting tone or contraction, which is herein described as lip ectropion. The muscle fibers of the retractors often penetrate and intertwine with the fibers of the orbicularis ori muscle forming the bulk of the lip. Decrease in the retractor tone causes the lip's mucous membrane to roll inward giving the appearance of smaller lips. This phenomenon is seen in patients with facial nerve palsy unilaterally.

The present inventor has found that because *Botulinum* toxin can cause a decrease in the volume of muscle fibers and decreased facial tone, directed *Botulinum* toxin injection into the lip can effect reduction in lip volume. Directed injection into the retractors of the lip as well as the orbicularis ori muscle also serves to reduce lip ectropion and mucous membrane exposure. By altering the volume of muscle within the lip structure, the lip becomes slightly deflated, without changing other soft tissue structures. The methods described herein are reversible with time and the effect can be altered by changing injection placement and dose. The methods described herein eliminate the need for incisional surgery to achieve these results.

Currently, smaller lips associated with age-related changes, or hereditary predisposition, can be considered disfiguring and a commercial enterprise has emerged yielding over $100,00,000 per year using injectable fillers such as collagen and hyaluronidate to increase lip bulk. The notion of reducing excessive lip size and bulk with *Botulinum* toxin preparations represents the converse intervention to volume enhancement with fillers and gives the facial plastic surgeon a useful tool for treating these deformities.

SUMMARY OF THE INVENTION

*Botulinum* toxin functions to create a denervative state when injected into orbicularis ori and surrounding lip muscle. By producing a denervative state, striated muscle tissue comprising a substantial portion of the lip proper undergoes atrophy, shrinking by as much as about 35%. The neurogenic muscular atrophy is reflected by shrinkage of upper and lower lips. The procedure is titratable by dose and reversible.

The present invention is directed, in certain emobodiments, to methods for reducing lip volume in a subject in need thereof. In preferred embodiments, the methods comprise administering a therapeutically effective amount of a pharmaceutical preparation of *Botulinum* toxin to the orbicularis oris muscle or any of the surrounding muscles which are part of the lip of said subject to thereby induce shrinkage of one or both of the upper and lower lips of said subject. Shrinkage may be characterized as a reduction in volume, mass, size or shape of the treated area. In certain preferred embodiments, the subjects to be treated suffer from a hypervolemic lip deformity or lip ectropion.

The pharmaceutical preparations of *Botulinum* toxin used in the methods of the invention may optionally comprise one or more sequestration agents as described below.

In preferred embodiments, the pharmaceutical preparation of *Botulinum* toxin comprises any combination of one or all of immunotypes A-G.

In still further embodiments, about 5 to about 2000 LD 50 units of *Botulinum* toxin are administered to said subject. More specifically, about 5, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about.730, about 740, about 750, about 760, about 770, about 780, about 790, about 800, about 810, about 820, about 830, about 840, about 850, about 860, about 870, about 880, about 890, about 900, about 910, about 920, about 930, about 940, about 950, about 960, about 970, about 980, about 990, about 1000, about 1010, about 1020, about 1030, about 1040, about 1050, about 1060, about 1070, about 1080, about 1090, about 1100, about 1110, about 1120, about 1130, about 1140, about 1150, about 1160, about 1170, about 1180, about 1190, about 1200, about 1210, about 1220, about 1230, about 1240, about 1250, about 1260, about 1270, about 1280, about 1290, about 1300, about 1310, about 1320, about 1330, about 1340, about 1350, about 1360, about 1370, about 1380, about 1390, about 1400, about 1410, about 1420, about 1430, about 1440, about 1450, about 1460, about 1470, about 1480, about 1490, about 1500, about 1510, about 1520, about 1530, about 1540, about 1550, about 1560, about 1570, about 1580, about 1590, about 1600, about 1610, about 1620, about 1630, about 1640, about 1650, about 1660, about 1670, about 1680, about 1690, about 1700, about 1710, about 1720, about 1730, about 1740, about 1750, about 1760, about 1770, about 1780, about 1790, about 1800, about 1810, about 1820, about 1830, about 1840, about 1850, about 1860, about 1870, about 1880, about 1890, about 1900, about 1910, about 1920, about 1930, about 1940, about 1950, about 1960, about 1970, about 1980, about 1990 or about 2000 LD 50 units of *Botulinum* toxin are administered to said subject.

In certain embodiments, the pharmaceutical preparation of *Botulinum* toxin is administered via transcutaneous, transdermal, or transmucosal injection.

In still further embodiments, the pharmaceutical preparation of *Botulinum* toxin is administered via multifocal injections at multiple sites around a desired site of treatment such as the lip, lower eyelid, upper eyelid, cheek, eyebrows, forehead or jowels.

The present invention is also directed to methods for reducing facial volume in a subject in need thereof, comprising administering a therapeutically effective amount of a pharmaceutical preparation of *Botulinum* toxin to the face of said subject to thereby induce a reduction in facial volume of said subject.

In certain embodiments, the reduction in facial volume is a reduction in muscle bulk below the eyelid, or above the eyelid, or the cheek, the eyebrows, or forehead or the jowels or any combination of these sites. In further embodiments, the reduction in facial volume is a reduction in bulges or prominences in or around the mouth, lips, gums, jowels, between the brows, the forehead, neck, eyebrows or cheeks. In still further embodiments, the methods may be used to reduce glabellar lines.

The present invention is also directed to methods for reducing facial muscle bulk and altering facial contour in a subject in need thereof, comprising administering a therapeutically effective amount of a pharmaceutical preparation of *Botulinum* toxin to the face of said subject to thereby induce a reduction in facial muscle bulk and an alteration in the facial contour of said subject. Facial contour is manifested by the presence of prominences, bulges, sags, folds, pock-marks, dimples or other topographical features. To alter facial contour is to make the contour structurally different or modified with respect to the initial characteristics of the contour being changed.

In certain embodiments, said reduction in facial muscle bulk and alteration in facial contour is a reduction in muscle bulk below the eyelid, the eyebrows or the forehead and is accompanied by a smoothing of the cheek or a smoothing of the jowels or a smoothing of the area which is treated. Such an application is in distinct contrast to rhytide (wrinkle reduction) as the injected region does not contain wrinkles or any other form of dynamic line, merely excessive tissue bulk.

In still further embodiments of the methods disclosed herein, subjects in need of any of the treatments described herein are selected prior to treatment based on a desire in the subject to eliminate or mitigate a deformity as described herein.

DETAILED DESCRIPTION

The invention described herein is directed, in certain embodiments, to methods of treating a category of lip deformity characterized by excessive bulk to the upper and/or lower lip with excessive exposure of mucous membrane. This condition is referred to as hypervolemic lip deformity or lip ectropion. Hypervolemic lip deformity can be perceived by the patient in the same vein as excessive prominence of the nose, jaw, forehead, eyebrows, or neck musculature. This condition can occur sporadically but occasionally is associated with specific populations. For example, African-Americans and other dark-skinned populations frequently have excessive lip bulk which can be reduced by the methods described herein. Sporadically, excessive lip bulk may be associated with jaw malocclusion or craniofacial abnormalities. Surgery to debulk or reduce lip volume can be painful and disfiguring. Consequently, few patients are interested in undergoing this ordeal.

The present inventor has demonstrated using an animal model that shrinkage of large paraspinal muscles may be obtained upon administration of pharmaceutical preparations of *Botulinum* toxin. This was observed using gross dissection and microscopic anatomy. This feature, combined with ease of injection of a *Botulinum* toxin, provides a facile method to treat hypervolemic lip deformity without surgery by multiple injections within the orbicularis ori muscle creating muscle fiber atrophy and hence decreased lip bulk. Additionally, decreased muscle tone associated with adjacent lip retractors functions to intort the lip (i.e. rotate the lip inward) further giving the impression of smaller lips. Such retractors include mentalis, zygomaticu, risorius, nasal labialis, Quadratus labii inferioris, and incisivus labii inferioris.

In one embodiment of the methods of the present invention, a patient is identified with hypervolemic lips who is desirous of lip size reduction at rest and during dynamic facial movements. Contraindications to the use of *Botulinum* toxin (wherein use of *Botulinum* toxin would be ruled out) include, for example, facial myopathy, myasthenia gravis and concurrent use of aminoglycoside antibiotics.

In one embodiment, *Botulinum* toxin in freeze-dried or liquid formulation is drawn into a syringe at a fixed dosage per 0.1 cc. Other dose dilutions are possible. Injections are made in multiple locations through the lip mucous membrane in at east 4 locations per lip. Lip retractors are not directly injected but may be injected if lip size is not adequately reduced by injecting the lip structure directly. Topical anesthetics such as 4% lidocaine cream or cetacaine spray may be used to reduce the discomfort of the procedure.

The effect does not occur immediately, but slowly over about 3 to about 5 weeks. Repeated injections are necessary over about 3 to about 4 month intervals. Asymmetry of mouth position during rest or dynamic movements may be addressed by "touch-up" injections after about 3 to about 5 weeks. The *Botulinum* toxin, when injected in multiple locations provides a method of muscle shrinkage which reverses over a 3-4 month period. Decreased resting muscle tone and contractility represent the muscular effect of *Botulinum* toxin due to the partially denervated state. Shrinkage of muscle fiber after point injection is seen in fiber after 4 weeks in table 1.

The invention described herein is also directed to methods for reducing facial muscle bulk and altering facial contour as well as methods of reducing facial volume.

A. Pharmaceutical Compositions Comprising *Botulinum* Toxin and a Sequestration Agent Pharmaceutical compositions comprising *Botulinum* neurotoxin and a sequestration agent are described in co-pending U.S. application Ser. No. 10/740,755 filed Dec. 22, 2003 which is hereby incorporated by reference into the present application in its entirety. Use of such pharmaceutical compositions comprising *Botulinum* toxin and a sequestration agent is contemplated in the methods of the present invention, but is not required.

As set forth in the co-pending '755 application, in one embodiment, the sequestration agent is present in an amount between 550 and 550,000 µg sequestration agent per 100 $LD_{50}$ units *Botulinum* toxin. In another embodiment, the sequestration agent is present in an amount between 550 and 5,500 µg sequestration agent per 100 $LD_{50}$ units *Botulinum* toxin. In a further embodiment, the sequestration agent is present in an amount between 5,500 and 13,000 µg sequestration agent per 100 $LD_{50}$ units *Botulinum* toxin. In a preferred embodiment, the sequestration agent is present in an amount between 13,000 and 50,500 µg sequestration agent per 100 $LD_{50}$ units *Botulinum* toxin. In a more preferred embodiment, the sequestration agent is present in an amount between 50,500 and 505,000 µg sequestration agent per 100 $LD_{50}$ units *Botulinum* toxin. In the most preferred embodiment, the sequestration agent is formulated as encapsulated microspheres in an amount between 50,500 and 90,500 µg sequestration agent per 100 $LD_{50}$ units *Botulinum* toxin.

In another embodiment, the methods may be practiced with a composition comprising *Botulinum* toxin and a sequestration agent, wherein the sequestration agent is present in an amount between 550 and 900,500 µg sequestration agent per 100 $LD_{50}$ units *Botulinum* toxin, wherein the albumin may be formulated as a solid albumin particle.

The *Botulinum* toxin of the present compositions may be selected from a variety of strains of *Clostridium Botulinum*. In a preferred embodiment, the compositions of the present invention comprises a *Botulinum* toxin selected from the group consisting of *Botulinum* toxin types A, B, C, D, E, F and G. In a preferred embodiment, the *Botulinum* toxin is *Botulinum* toxin type A. In a more preferred embodiment, the *Botulinum* toxin is *Botulinum* toxin type A from the Hall strain of *Clostridium Botulinum*.

In another embodiment, the compositions of the present invention comprise a *Botulinum* toxin that consists essentially of fractionated-light-chain *Botulinum* toxin. In yet another embodiment, the *Botulinum* toxin consists essentially of a mixture of hybrid and chain-translocated forms of *Botulinum* toxin. In a further embodiment, the *Botulinum* toxin consists essentially of chimeric forms of *Botulinum* toxin. Although the present invention may utilize any *Botulinum* toxin, *Botulinum* toxin fragment that retains neurotoxic activity, *Botulinum* toxin chimeras and hybrids, chemically-modified *Botulinum* toxin, and specific activities well known to those of ordinary skill in the art, in one embodiment the *Botulinum* toxin is purified to a specific activity greater than or equal to about 20 $LD_{50}$ units per nanogram *Botulinum* toxin.

In certain embodiments, the compositions of *Botulinum* toxin and a sequestration agent are such that the ratio of $LD_{50}$ units of *Botulinum* toxin to µg sequestration agent is less than or equal to about 0.2 for *Botulinum* toxin type A and is less than or equal to about 10 for *Botulinum* toxin type B.

The compositions used in the methods of the present invention, in addition to comprising a *Botulinum* toxin and optionally a sequestration agent, may further comprise a pharmaceutically acceptable carrier and/or zinc and/or a zinc salt. In one embodiment, the *Botulinum* toxin is noncovalently bound to the a sequestration agent. In another embodiment, the *Botulinum* toxin is covalently bound to the sequestration agent.

The methods of the present invention may be practiced using compositions of a *Botulinum* toxin and optionally, a sequestration agent, wherein the sequestration agent is selected from the group consisting of: proteins, lipids and carbohydrates. In a preferred embodiment, the sequestration agent is albumin, collagen, epinephrine or hyaluronate. In a more preferred embodiment, the sequestration agent is hyaluronate. In the most preferred embodiment, the sequestration agent is albumin.

The methods of the present invention may also be practiced using compositions comprising a *Botulinum* toxin and, optionally a sequestration agent, wherein the sequestration agent is an albumin, preferably human serum albumin. Furthermore, in one embodiment, the albumin of the present compositions is recombinantly produced. In one embodiment, the albumin is present in an amount between 550 and 5,500 µg albumin per 100 $LD_{50}$ units *Botulinum* toxin. In a further embodiment, albumin is present in an amount between 5,500 and 13,000 µg albumin per 100 $LD_{50}$ units *Botulinum* toxin. In a preferred embodiment, albumin is present in an amount between 13,000 and 50,500 µg albumin per 100 $LD_{50}$ units *Botulinum* toxin. In a more preferred embodiment, albumin is present in an amount between 50,500 and 505,000 µg albumin per 100 $LD_{50}$ units *Botulinum* toxin. In a most preferred embodiment, albumin is formulated as encapsulated microspheres in an amount between 50,500 and 90,500 µg albumin per 100 $LD_{50}$ units *Botulinum* toxin.

In one embodiment of the present invention, the methods of the present invention may be practiced using compositions comprising a *Botulinum* toxin and, optionally, at least one sequestration agent. In a preferred embodiment, the methods of the present invention may be practiced using compositions comprising a *Botulinum* toxin and albumin and further comprising one or more additional sequestration agents.

B. Definitions

As used herein, "effective amount" is an amount sufficient to produce a therapeutic response. An effective amount may be determined with dose escalation studies in open-labeled clinical trials or bin studies with blinded trials.

As used herein, a "subject in need thereof" is any patient suffering from a deformity arising from excessive tissue bulk or muscle bulk or tissue volume or muscle volume.

As used herein, a "deformity" is any physical blemish, imperfection or distortion caused by or associated with excessive tissue bulk or muscle bulk or tissue volume or muscle volume, as perceived by the subject having the deformity.

As used herein, one LD 50 Unit of *Botulinum* toxin is the dose necessary to kill 50% of a population of about 20 gram to about 30 gram Swiss-Webster mice.

As used herein, "sequestration agent" means an agent that enhances localization and/or retention of the *Botulinum* toxin to the site of administration.

The following examples are meant to illustrate the methods of the invention and are in no way intended to limit the scope of the invention.

EXAMPLES

Example 1

Case Description of Reduction of Hypervolemic Lip Size and Volume using *Botulinum* Toxin AC is a 49 year old woman with a life-long history of excessive lip size. AC stated that she found this condition disfiguring and desired lip volume reduction. AC had worked as a psychologist and felt that this feature (excessive lip size) distorted her ability to communicate with patients and detracted from her personal appearance.

The option of using *Botulinum* toxin as a method to shrink the muscle fiber comprising a major component of her excessive lip volume was offered and she expressed the desire to proceed with this intervention. After explaining possible side effects including mouth movement asymmetry and possible temporary drooling, she wished to proceed.

About 20 Units of *Botulinum* toxin type A were injected at four locations within the upper lip and about 20 Units of *Botulinum* toxin type A were injected into multiple locations in the lower lip. After about 3 weeks, the patient noted considerable reduction in lip size and less exposure of lip mucous membrane. The effect was noted to last for about 3-4 months. By shrinking muscle volume in AC's lips by creating neurogenic atrophy induced by *Botulinum* toxin, lip volume and contour were altered and disfigurement mitigated.

Example 2

Influence of Injection Doses on Muscle Fiber Size using *Botulinum* Toxin Type A Using doses of *Botulinum* toxin type A varying from about 1.25 Units per injection point to about 15 Units per injection point, the influence of injection doses on muscle fiber size was examined and the results are shown in table 1. The listed doses represent use of *Botulinum* toxin type A. For *Botulinum* toxin type B, 100-500 Units are anticipated per injection point. Other formulations can be selected for dose using regional denervation bioassays comparing the potency of the preparation with that of *Botulinum* toxin type A formulated as BOTOX™ or PURTOX (see table 1). In Table 1, average muscle fiber cross-sectional diameter is shown in microns (with standard deviation) at increasing distances from the point of injection for PURTOX dose escalations. Comparable denervation results were obtained with BOTOX™ (n=100, per biopsy location, Bioquant II Fiber counter).

TABLE 1

Dose and Distance (mm) from Injection Site

| Dose | 0 mm | 15 mm | 30 mm | 45 mm | Gluteus Max | Quadricepts | Animal No. |
|---|---|---|---|---|---|---|---|
| 15 U | 23.53** | 26.60** | 28.42** | FA | 44.02 | 31.59 | B23 |
|  | 15.68 | 17.08++ | 16.27++ |  | 21.37+ | 14.34 |  |
| 10 U | 30.30* | 28.29* | 25.42** | 26.06** | 32.29 | 35.41 | B20 |
|  | 18.65 | 22.80++ | 17.90++ | 19.72++ | 12.80 | 15.34 |  |
| 5 U | 27.58** | 29.88* | 36.70 | 35.44 | 35.28 | 35.27 | B9 |
|  | 13.35 | 15.54++ | 15.92 | 15.31 | 14.14 | 12.73 |  |
| 2.5 U | 26.65** | 31.9 | 34.6 | 39.77 | 35.09 | 34.03 | B27 |
|  | 13.96 | 12.50 | 15.19 | 14.20 | 14.54 | 12.23 |  |
| 1.25 U | 33.4 | 34.18 | FD | 36.37 | 37.52 | FD | B14 |
|  | 13.75 | 12.99 |  | 13.86 | 12.86 |  |  |
| excipient | 36 | 35.08 | 32.15 | 35.99 | 35.27 | 38.8 | B35 |
|  | 13.36 | 10.5 | 10.74 | 12.76 | 15.57 | 16.36 |  |

Example 3

Method of Reducing Facial Muscle Bulk and Altering Facial Contour

A patient is identified with increased muscle bulk below the eyelids. The patient is selected for treatment with *Botulinum* toxin based on her desire to reduce the facial muscle bulk displayed below her eyelids. Multifocal injections of about 20 Units of *Botulinum* type A in a pharmaceutical composition comprising a sequestration agent are administered to the patient. After about three weeks, the patient notes a decrease in facial muscle bulk below her eyelids which is accompanied by an altered facial contour manifested by a smoother, less prominent, appearance of the skin below the eyelids.

The invention claimed is:

1. A method for reducing lip volume in a subject in need of reduced lip volume, comprising the steps of: assessing lip volume, administering a therapeutically effective amount of a pharmaceutical preparation of *Botulinum* toxin to one or both of the lips of said subject to thereby induce reduced lip volume in one or both of the upper and lower lips of said subject, and assessing lip volume after said administration.

2. The method of claim 1, wherein said pharmaceutical preparation is administered to the orbicularis oris muscle of said subject.

3. The method of claim 1, wherein said pharmaceutical preparation is administered to the lip retractors.

4. The method of claim 1, wherein said subject has a hypervolemic lip deformity.

5. The method of claim 1, wherein the pharmaceutical preparation of *Botulinum* toxin comprises any combination of more than one of immunotypes A, B, C, D, B, F and G.

6. The method of claim 1, wherein about 5 to about 2000 Lethal Dose$_{50}$ (LD$_{50}$) units of Botulinum toxin are administered to said subject.

7. The method of claim 1, wherein the pharmaceutical preparation of *Botulinum* toxin is administered via transcutaneous or transmucosal injection.

8. The method of claim 1, wherein the pharmaceutical preparation of *Botulinum* toxin is administered via multifocal injection.

* * * * *